(12) United States Patent
Allende

(10) Patent No.: US 6,342,052 B1
(45) Date of Patent: Jan. 29, 2002

(54) ANORECTAL APPARATUS

(75) Inventor: Hector D. Allende, 209 Tower, San Antonio, TX (US) 78232

(73) Assignee: Hector D. Allende, San Antonio, TX (US)

(*) Notice: Subject to any disclaimer, the term of this patent is extended or adjusted under 35 U.S.C. 154(b) by 0 days.

(21) Appl. No.: 09/431,786

(22) Filed: Nov. 2, 1999

(51) Int. Cl.$^7$ ................................................ A61M 1/00
(52) U.S. Cl. ...................... 604/540; 604/276; 600/582; 600/29
(58) Field of Search ............................ 604/8, 9, 10, 328, 604/329, 327, 514, 515, 517, 540, 276; 600/574, 582, 29, 30; 623/12

(56) References Cited

U.S. PATENT DOCUMENTS

| 724,913 A | 4/1903 | Montgomery |
| 1,080,934 A | 12/1913 | W. L. Shackleford |
| 1,711,294 A | 4/1929 | Weitzner |
| 2,754,822 A | 7/1956 | Emelock ...................... 128/264 |
| 3,575,160 A | 4/1971 | Vass ............................. 128/2 R |
| 3,906,948 A | 9/1975 | Vass ............................. 128/245 |
| 4,137,918 A | 2/1979 | Bogert ........................ 128/245 |
| 4,634,421 A | * 1/1987 | Hegemann .................... 604/34 |
| 4,781,176 A | 11/1988 | Ravo ............................ 600/30 |
| 4,943,285 A | 7/1990 | Hawks ........................ 604/275 |
| 4,969,902 A | 11/1990 | Ravo ............................ 623/12 |
| 4,986,822 A | 1/1991 | Anderson .................... 604/276 |
| 5,059,169 A | * 10/1991 | Zilber ............................ 604/8 |
| 5,578,017 A | * 11/1996 | Aguilar ....................... 604/275 |
| 5,782,745 A | 7/1998 | Benderev ..................... 600/30 |

* cited by examiner

Primary Examiner—Richard K. Seidel
Assistant Examiner—Kevin C. Sirmons
(74) Attorney, Agent, or Firm—Christopher L. Makay

(57) ABSTRACT

An anorectal apparatus for insertion in an anorectum including a body and a passageway extending through the body. The anorectal apparatus protects the anal canal, the perianus, and the perineum from direct and prolonged contact with fecal material such that the anorectal apparatus is continuously inserted in the anorectum. Inasmuch, the body includes a contact head in engagement with the anorectum and a flange, extending from the contact head, in engagement with the anal canal. Fecal material is thus discharged from the rectum, via the passageway, by traveling from the contact head through the flange. It should be added that the anorectal apparatus is preferably shaped to accommodate the biological contouring of the anorectum.

21 Claims, 4 Drawing Sheets

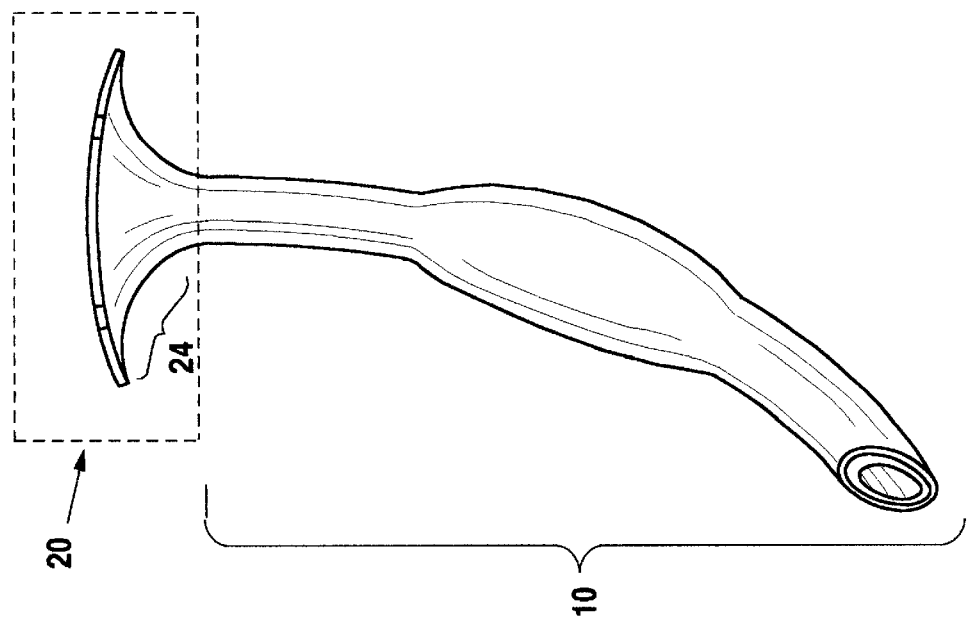
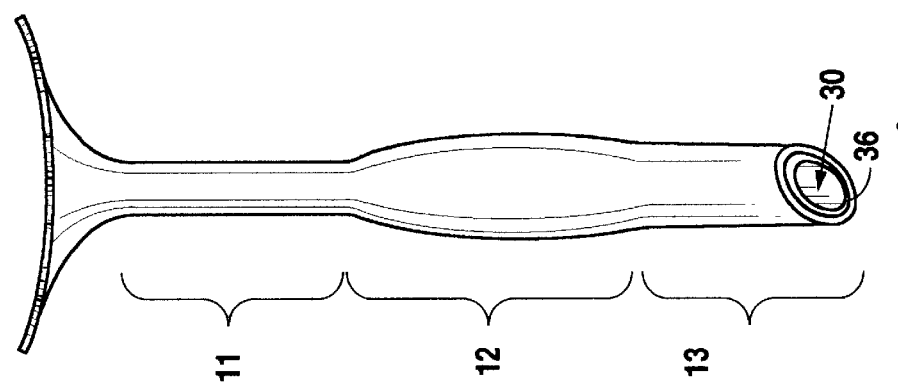
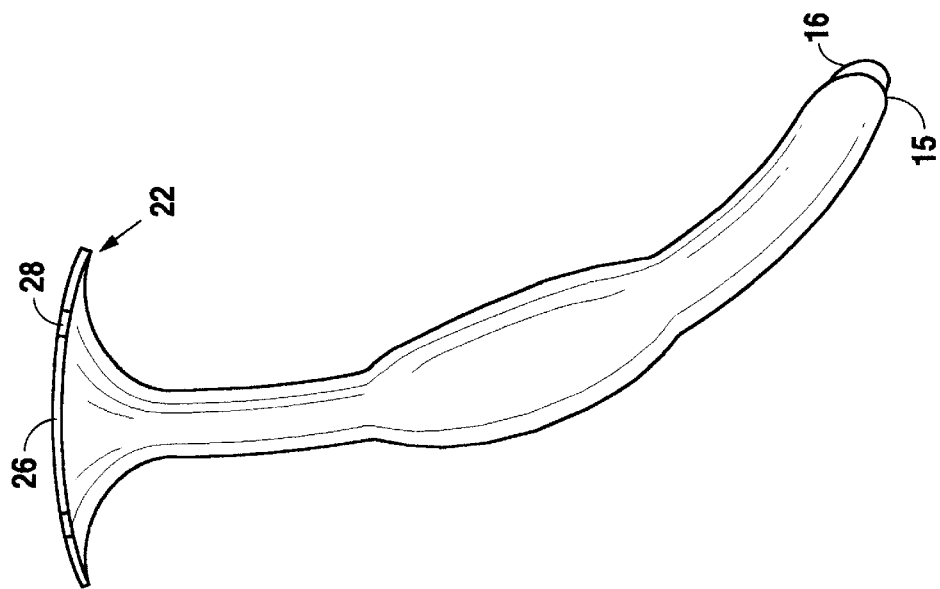

ANORECTAL APPARATUS

BACKGROUND OF THE INVENTION

1. Field of the Invention

The present invention generally relates to equipment for collecting fecal material and, more particularly, but not by way of limitation, to a rectal catheter.

2. Description of the Related Art

Patients with bowel movements that are frequent or left unclean even for a short period often suffer from irritation along the anal canal, perianus, and perineum ranging from rashes to ulcers. Further stool passings with such irritations can inflict pain to an already very ill patient as well as exacerbate an existing unpleasant condition and incurring greater medical expenses. Moreover, if left untreated, continued bowel movements have been medically shown to have an adverse impact on a patient's clinical outcome by increasing the possibility of morbidity and mortality.

Currently, various related devices are designed for alleviating incontinence or for obtaining biomedical samples. These devices are typically for periodic insertion along the rectum and anal canal and are not designed for prolonged insertion.

Accordingly, there is a long felt need for an anorectal device for continuous insertion along and for protection of the anal canal, perianus, and perineum from unfavorable irritation caused by direct and prolonged contact with fecal material.

SUMMARY OF THE INVENTION

In accordance with the present invention, an anorectal apparatus for insertion in an anorectum including a body and a passageway extending through the body. The body includes a contact head in engagement with the anorectum and a flange, extending from the contact head, in engagement with the anal canal. Fecal material is thus discharged from the rectum, via the passageway, by traveling from the contact head through the flange.

The anorectal apparatus protects the anal canal, the perianus, and the perineum from direct and prolonged contact with fecal material such that the anorectal apparatus is continuously inserted in the anorectum. It should be added that the anorectal apparatus is preferably shaped to accommodate the biological contouring of the anorectum.

Specifically, the flange includes a sphincter contact member secured to the contact head whereby fecal material from the contact head travels through the passageway within the sphincter contact member. An anal verge stopper member extending substantially downwardly from the sphincter contact member is also provided whereby fecal material from the sphincter contact member travels thorough the passageway within the anal verge stopper member. The flange further includes an applicator member extending substantially downwardly from the anal verge stopper member whereby fecal material from the anal verge stopper member travels from the anal verge stopper member through the passageway within the applicator member.

The contact head includes a contact membrane for facilitating the gathering of fecal material whereby the passageway is in communication with the contact membrane to thus receive fecal material from the contact membrane. The contact membrane, in turn, includes a seat for anchoring the anorectal apparatus against the anorectum. The contact membrane further includes a plurality of anchoring elements, each anchoring element extending outwardly from the contact membrane for enhancing anchoring contact between the contact membrane and the anorectum. Moreover, a plurality of elemental notches are provided between the anchoring elements for increasing the surface area by which the anorectum contacts and attaches to the anchoring elements. In particular, the anchoring elements and the elemental notches are each configured for cooperative engagement with the columns of Morgani.

In accordance with the present invention, a method for inserting an apparatus in an anorectum includes inserting an anorectal apparatus in an anorectum for engagement with fecal material within the rectum and discharging fecal material from the rectum via the anorectal apparatus. Specifically, the anorectal apparatus is inserted in an anorectum by passing a contact membrane of the anorectal apparatus through the anal canal and positioning the contact membrane within the anorectum. It should also be added that the anorectal apparatus is preferably shaped to accommodate the biological contouring of the anorectum.

Passing the contact membrane of the apparatus through the anal canal includes resting an anal verge stopper member of the anorectal apparatus along the anal verge. Positioning the contact membrane includes anchoring a seat of the contact membrane against the anorectum. Positioning the contact membrane further includes increasing the surface area by which the rectum contacts and attaches to the anchoring elements via a plurality of elemental notches provided between anchoring elements.

Discharging fecal material from the rectum via the anorectal apparatus includes gathering fecal material from the rectum via the contact membrane, drawing fecal material through a passageway provided by the apparatus, and discharging fecal material from the flange.

It is therefore an object of the present invention to provide an anorectal apparatus and associated methods for protection of the anal canal, perianus, and perineum from unfavorable irritation caused by direct and prolonged contact with fecal material.

It is a further object of the present invention to provide an anorectal apparatus optimally configured for continuous insertion along the anal canal, perianus, and perineum.

Still other objects, features, and advantages of the present invention will become evident to those skilled in the art in light of the following.

BRIEF DESCRIPTION OF THE DRAWINGS

FIG. 2 shows an anorectal apparatus from the side. FIG. 2a illustrates the anorectal apparatus along the left side. FIG. 2b illustrates the anorectal apparatus along the front side. FIG. 2c illustrates the anorectal apparatus along the right side.

FIG. 4 shows an anorectal apparatus from the top and the bottom.

DETAILED DESCRIPTION OF THE PREFERRED EMBODIMENT

Figure 1:
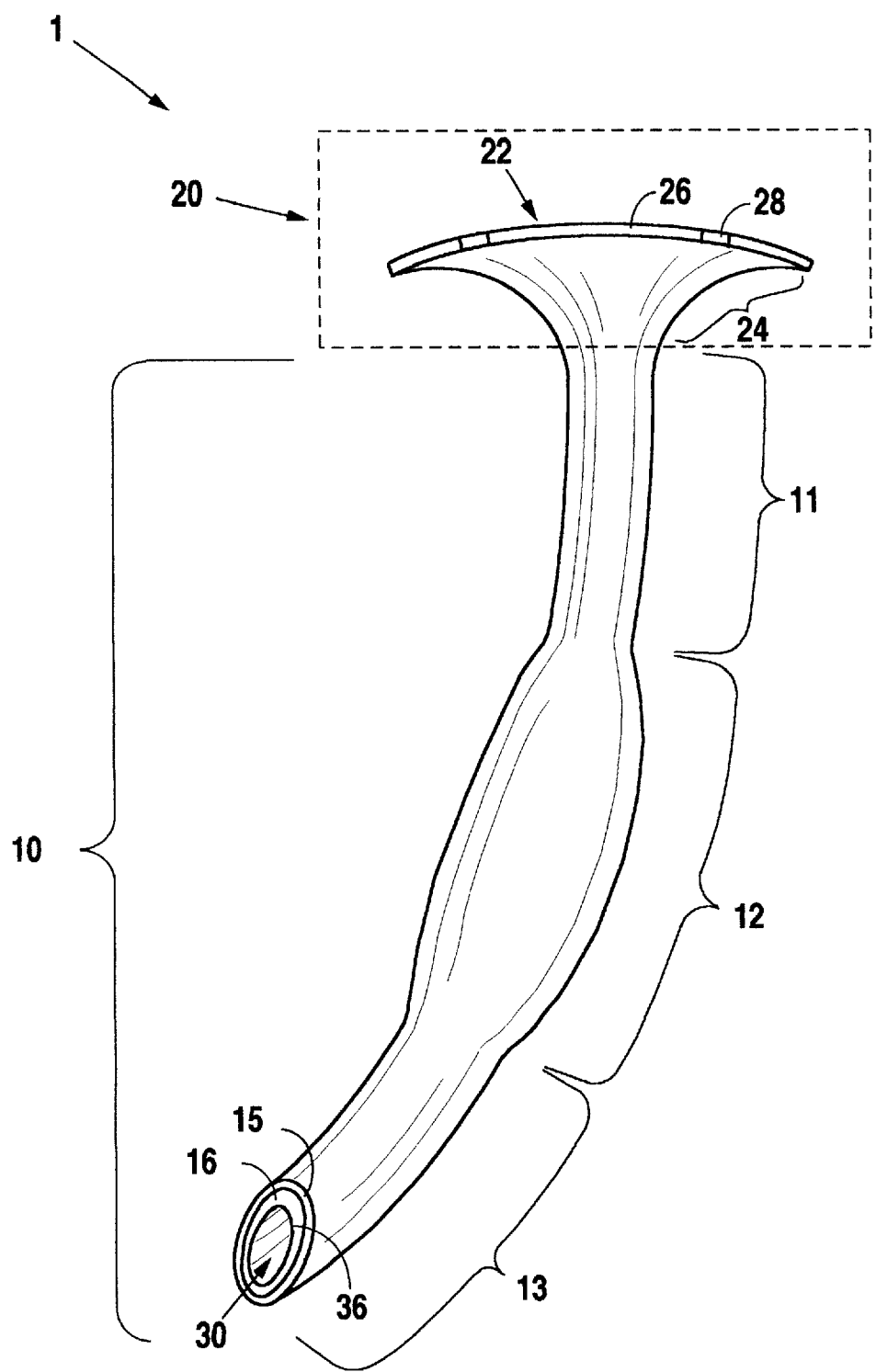
FIG. 1 is a side view illustrating an anorectal apparatus according to the preferred embodiment for continuous insertion along and for protection of the anal canal, perianus, and perineum.
Figure 3:
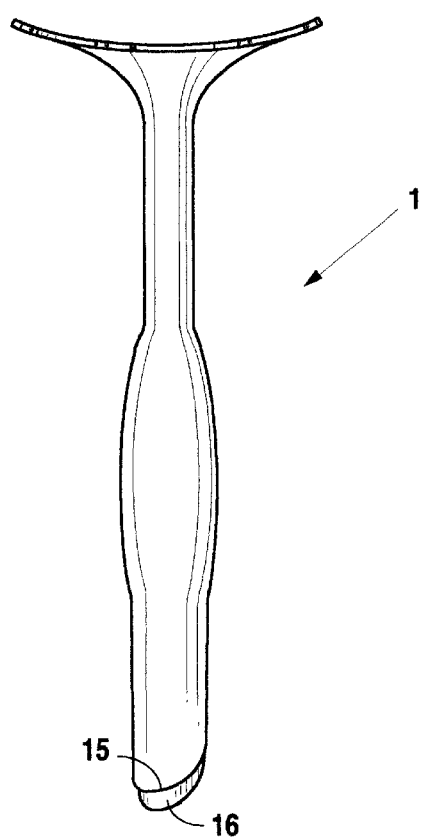
FIG. 3 is a side view illustrating the anorectal apparatus of FIG. 2 along the back side.

As required, detailed embodiments of the present invention are disclosed herein, however, it is to be understood that the disclosed embodiments are merely exemplary of the invention, which may be embodied in various forms, the figures are not necessarily to scale, and some features may be exaggerated to show details of particular components or steps.

FIGS. 1–4 illustrate an anorectal apparatus 1 according to the preferred embodiment for insertion into the anal canal and rectum of a patient. The preferred anorectal apparatus 1 is formed as a single piece although those of ordinary skill in the art will recognize that the anorectal apparatus may be constructed from a plurality of pieces.

Generally, the anorectal apparatus 1 includes a contact head 20 for engagement with the rectum and interior anal sphincters. A flange 10 extending downwardly from the contact head 20 is provided for engagement with the anal canal and external anal sphincters. The anorectal apparatus 1 includes a material passageway 30 extending through the anorectal apparatus 1 for passing fecal material from the contact head 20 through the flange 10. Therefore, operatively, the anorectal apparatus 1 is inserted through the anal canal and rectum so that the contact head 20 is seated above the internal anal sphincter within the rectum and the flange 10 extends outwardly from the anal canal, thereby allowing the discharge of fecal material through the anorectal apparatus 1 without contacting the patient.

As such, the flange 10 preferably comprises a sphincter contact member 11 just below and secured to the contact head 10, an anal verge stopper member 12 extending substantially downwardly from the sphincter contact member 11, and an applicator member 13 extending substantially downwardly from the anal verge stopper member 12. Thus, the sphincter contact member 10, the anal verge stopper member 12, and the applicator member 13 are all linked and in communication with one another so that the material passageway 30 passes though each member along the length of the flange 10. In addition, because it must remain lodged within the relatively narrow anal canal as well as potentially facilitate connection with other instrumentation, the flange 10 is preferably constructed of a non-biologically irritating and flexible material, such as plastic or rubber.

Although those of ordinary skill in the art may contemplate other suitable shapes, it must be emphasized that the sphincter contact member 11, the anal verge stopper member 12, and the applicator member 13 all maintain a shape for facilitating long term insertion within the rectum and anal canal without discomfort to the patient. In particular, the sphincter contact member 11 is preferably narrow to accommodate the relatively narrow contouring of the anal canal and external anal sphincters. The anal verge stopper member 12 is preferably bulbous in shape so that the anal verge stopper member 12 rests along the anal verge, thereby preventing an unfavorable condition where the anorectal apparatus 1 completely enters and remains lodged within the rectum. The applicator member 13 is preferably narrow and tapered for facilitating discharge of fecal material from the anorectal apparatus 1 via a discharge tip 15.

Moreover, the preferred applicator member 13 features a connection groove 16 for facilitating connection with various other instrumentation, such as a fecal material collector bag (not shown) or a tube (not shown). The connector groove 16 is configured to facilitate any standard connector thereon, such connectors as a PHARMASEAL "Plastic Tubing Connector 5 in 1" manufactured by Baxter Healthcare Corporation of Valencia, Calif. as well as a "Sims Connector" manufactured by Busse of Haupauge, N.Y. As such, one embodiment contemplates linking the anorectal apparatus 1 with a pump (not shown) via the connection groove 16 for drawing fecal material from the rectum through the anorectal apparatus 1.

The contact head 20 includes a contact membrane 22 generally for facilitating the gathering of fecal material, whereby the flange 10 extends downwardly from the contact membrane 22 and the material passageway 30 within the flange 10 is in communication with the contact membrane 22. The contact membrane 22 is preferably constructed of a pliant and non-biologically irritating material, such as plastic or rubber, so that the contact membrane 22 can collapse while traveling through the relatively narrow anal canal and expand outwardly before finally resting above the internal anal sphincter.

Furthermore, although those of ordinary skill in the art may contemplate other suitable shapes, it must be emphasized that the contact membrane 22 maintains a shape for facilitating long term insertion within the rectum without discomfort to the patient. Specifically, the contact membrane 22 preferably comprises a funnel-like shape for directing fecal material into the flange 10 as well as for resting above the internal anal sphincter. As such, the contact membrane 22 includes a seat 24 for anchoring the anorectal apparatus 1 against the internal anal sphincter.

The contact membrane 22 further includes a plurality of anchoring elements 26 extending outwardly from the contact membrane 22 for enhancing anchoring contact between the contact membrane 22 and the rectum. Additionally, elemental notches 28 are provided between each anchoring element 26 to allow flesh and mucosa associated with the rectum to push up through the elemental notches 28 so as to move above and cling to the anchoring elements 26, thereby increasing the surface area by which the rectum can contact and attach to the anchoring elements 26. In the preferred embodiment, the shape of the anchoring elements 26 and the depth of the elemental notches 28 are configured for cooperative engagement with the columns of Morgani, especially between eight and fourteen columns of Morgani.

Figures 4A, 4B:
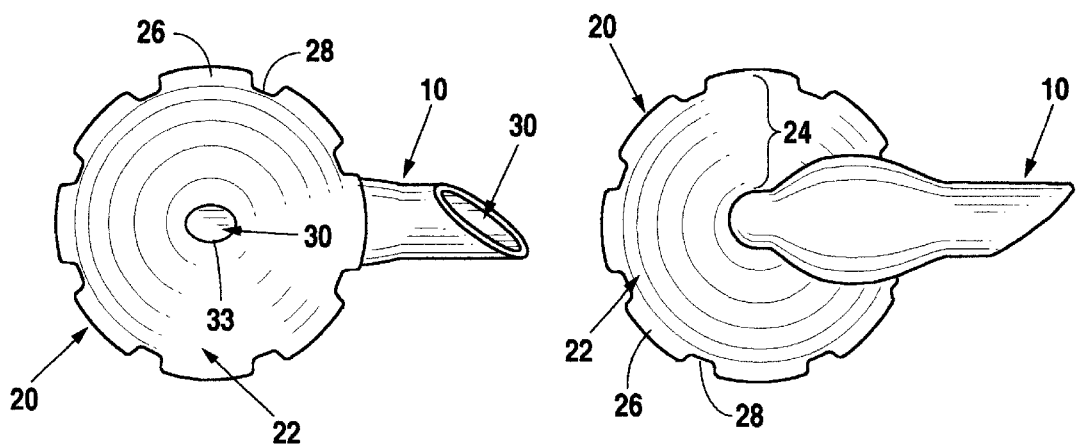
FIG. 4a illustrates a top view of the anorectal apparatus.
FIG. 4b illustrates a bottom view of the anorectal apparatus.
Figure 5:
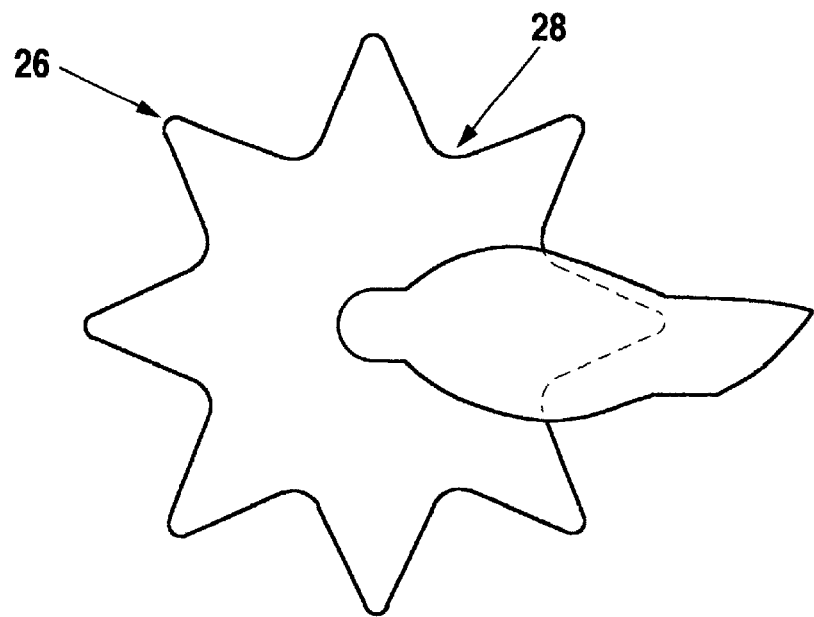
FIG. 5 is a bottom view of an anorectal apparatus featuring one embodiment for the anchoring elements.
Figure 6:
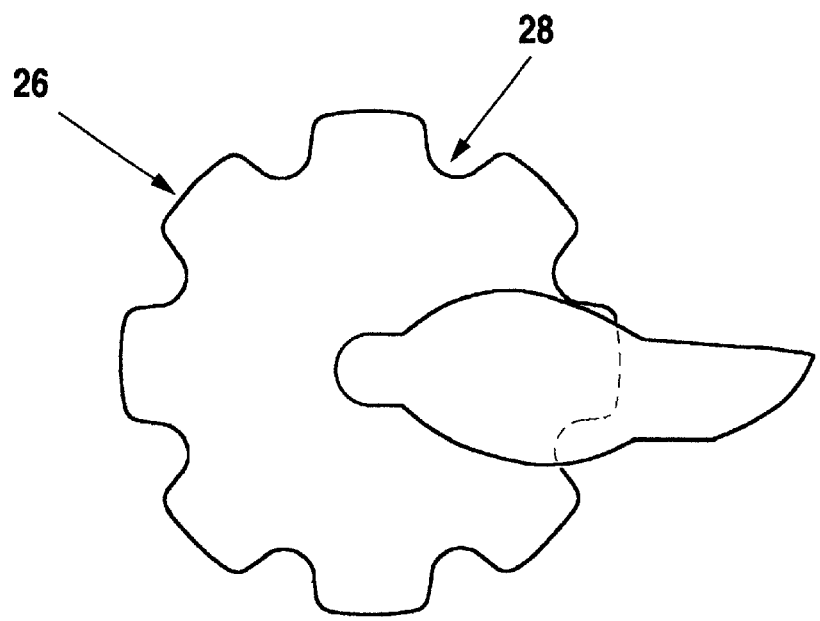
FIG. 6 is a bottom view of an anorectal apparatus featuring another embodiment for the anchoring elements.

Various embodiments for the anchoring elements 26 are shown in FIGS. 4–6. In FIG. 4, the anchoring elements 26 maintain a "scallop" shape for engagement with the columns of Morgani. The anchoring elements 26 in FIG. 1 are configured in a "flower petal" shape for engagement with the columns of Morgani. The anchoring elements 26 of FIG. 6 maintain a scallop shape similar to that of FIG. 4 except the anchoring elements 26 of FIG. 6 extend further outward than those of FIG. 4 and, thus, the corresponding elemental notches 28 are deeper, thereby providing enhanced engagement with the columns of Morgani.

The material passageway 30 includes a material passageway inlet 33, shown in FIG. 4a, in communication with the contact membrane 22, for receiving fecal material from the rectum. The material passageway 30 includes a material passageway outlet 36, shown in FIG. 1, in communication with the discharge tip 15, for discharging fecal material from the anorectal apparatus 1. Although those of ordinary skill in the art may contemplate other suitable shapes, it must be emphasized that the material passageway 30 maintains a shape for facilitating long term insertion within the rectum and anal canal without discomfort to the patient. Specifically, in the preferred embodiment, the material passageway 30 comprises an elliptical shape, generally resembling the shape of the anal canal, for directing fecal material through the flange 10.

Therefore, in operation, the anorectal apparatus 1 is inserted up the rectum, the contact membrane 22 being inserted first, through the anal canal until the anal verge stopper member 12 sufficiently rests against the anal verge. Fecal material is thus gathered from the rectum by the contact membrane 22, enters the material passageway inlet 33, travels through the flange 10, and exits through the material passageway outlet 36. Although those of ordinary skill in the art will recognize other suitable means for drawing fecal material through the anorectal apparatus 1 such as pump, fecal material is preferably drawn though the anorectal apparatus 1 by gravitational forces. As such, the anorectal apparatus 1 may be continuously inserted along the rectum and anal canal, thereby protecting the rectum and anal canal from unfavorable irritation caused by direct and prolonged contact with fecal material.

Although the present invention has been described in terms of the foregoing embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing description, rather, it is defined only by the claims that follow.

I claim:

1. An apparatus insertable into an anorectum for discharging fecal material, comprising:
   a body;
   a passageway extending through the body;
   the body comprising a contact head insertable through an anal canal and engageable with a rectum and a flange extending from the contact head and engageable with the anal canal, whereby fecal material is discharged, via the passageway, from the rectum by traveling from the contact head through the flange;
   the contact head comprising a contact membrane for facilitating the gathering of fecal material, whereby the passageway is in communication with the contact membrane for receiving fecal material from the contact membrane; and
   the contact membrane comprising a plurality of anchoring elements, whereby each anchoring element extends outwardly from the contact membrane for enhancing anchoring contact between the contact membrane and the anorectum.

2. The apparatus according to claim 1 wherein the apparatus is shaped to accommodate the biological contouring of the anorectum.

3. The apparatus according to claim 1 wherein the contact head is movable between a collapsed position permitting travel through the anal canal and an expanded position permitting engagement with the rectum.

4. The apparatus according to claim 1 wherein the apparatus protects the anal canal, perianus, and perineum from direct and prolonged contact with fecal material.

5. The apparatus according to claim 1 wherein the flange comprises a sphincter contact member secured to the contact head, whereby fecal material from the contact head travels through the passageway within the sphincter contact member.

6. The apparatus according to claim 5 wherein the sphincter contact member is shaped to accommodate the contouring of the anal canal and anus.

7. The apparatus according to claim 5 wherein the flange further comprises an anal verge stopper member extending substantially downwardly from the sphincter contact member, whereby fecal material from the sphincter contact member travels through the passageway within the anal verge stopper member.

8. The apparatus according to claim 7 wherein the anal verge contact member is bulbous in shape to allow the anal verge contact member to rest along the anal verge, thereby preventing the apparatus from completely entering the rectum.

9. The apparatus according to claim 7 wherein the flange further comprises an applicator member extending substantially downwardly from the anal verge stopper member, whereby fecal material from the anal verge stopper member travels through the passageway within the applicator member.

10. The apparatus according to claim 9 wherein the anal verge contact member is tapered for facilitating discharge of fecal material.

11. The apparatus according to claim 1 wherein the contact membrane includes a seat for anchoring the apparatus against the anorectum.

12. The apparatus according to claim 1 wherein the contact membrane further includes a plurality of elemental notches provided between the anchoring elements for increasing the surface area by which the anorectum contacts and attaches to the anchoring elements.

13. The apparatus according to claim 12 wherein the anchoring elements and elemental notches are each configured for cooperative engagement with the columns of Morgani.

14. The apparatus according to claim 13 wherein the anchoring elements and elemental notches are each configured for cooperative engagement with eight to fourteen columns of Morgani.

15. A method for discharging fecal material, comprising the steps of:
    providing an apparatus, comprising:
      a body including a contact head insertable through an anal canal and engageable with a rectum and a flange extending from the contact head and engageable with the anal canal, and
      a passageway extending through the body;
    inserting the apparatus in an anorectum for engagement with fecal material therein, comprising:
      passing a contact membrane of the apparatus through the anal canal,
      resting an anal verge stopper member of the apparatus along the anal verge,
      anchoring a seat of the contact membrane against the anorectum, and
      anchoring the contact membrane to the anorectum via a plurality of anchoring elements provided by the contact membrane; and
    discharging fecal material from the rectum via the apparatus.

16. The method according to claim 15 wherein the step of inserting the apparatus in an anorectum further comprises the step of increasing the surface area by which the anorectum contacts and attaches to the anchoring elements via a plurality of elemental notches provided between the anchoring elements.

17. The method according to claim 15 wherein the step of discharging fecal material from the rectum via the apparatus comprises the steps of:
    gathering fecal material from the rectum via the contact membrane;

drawing the fecal material through a passageway provided by the apparatus; and discharging fecal material from the flange.

18. The method according to claim 17 wherein the step of drawing fecal material through a passageway provided by the apparatus comprises the step of drawing fecal material via gravitational forces.

19. The method according to claim 18 wherein the contact head is movable between a collapsed position permitting travel through the anal canal and an expanded position permitting engagement with the rectum.

20. The method according to claim 15, further comprising the step of shaping the apparatus to accommodate the biological contouring of the anorectum.

21. The method according to claim 15, wherein insertion of the apparatus protects the anal canal, perianus, and perineum from prolonged contact with fecal material.

* * * * *